United States Patent [19]

Okano et al.

[11] 4,402,326
[45] Sep. 6, 1983

[54] OCCLUSION PRESSURE IMAGE SYSTEM

[75] Inventors: Michiaki Okano, Uji; Shuhei Furuichi, Shiga, both of Japan

[73] Assignee: Kabushiki Kaisha Morita Seisakusho, Kyoto, Japan

[21] Appl. No.: 258,646

[22] Filed: Apr. 29, 1981

[30] Foreign Application Priority Data

May 2, 1980 [JP] Japan .................................. 55-59278

[51] Int. Cl.³ .............................................. A61C 3/00
[52] U.S. Cl. .................................... 128/774; 128/776; 128/777; 433/68
[58] Field of Search ............... 73/862.68, 172; 128/17, 128/19, 774, 776, 773; 433/68, 69

[56] References Cited

U.S. PATENT DOCUMENTS

| | | | |
|---|---|---|---|
| 3,349,489 | 10/1967 | Shackelford | 433/68 |
| 3,883,954 | 5/1975 | Simmering et al. | 128/776 |
| 3,983,865 | 10/1976 | Shepard | 128/777 |
| 4,250,894 | 2/1981 | Frei et al. | 128/774 |

Primary Examiner—Richard J. Apley
Assistant Examiner—George Yanulis
Attorney, Agent, or Firm—Koda and Androlia

[57] ABSTRACT

This disclosure relates to an occlusion pressure image display system which is designed to make visual display of the output signals of the occlusion pressure sensor in the form of a black-and-white or color brilliance image on a CRT screen. The system comprises in combination, a novel occlusion pressure sensor designed to convert information on the occlusion pressure of the teeth into electric signal output by mere biting with the teeth and a raster scanning type CRT display.

29 Claims, 21 Drawing Figures

FIG.16
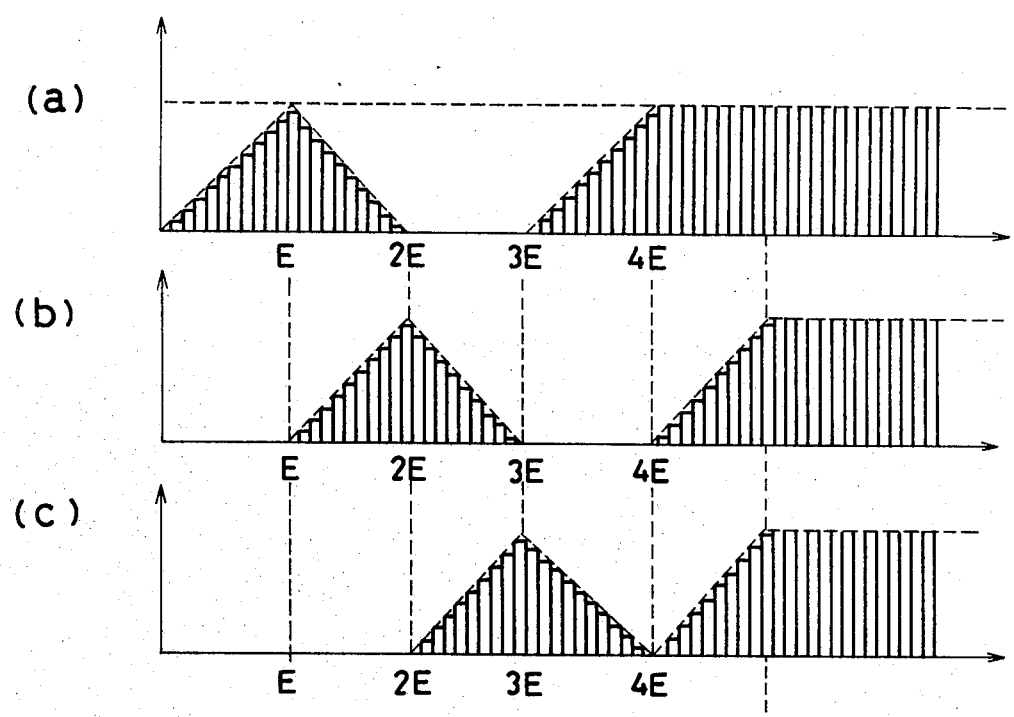
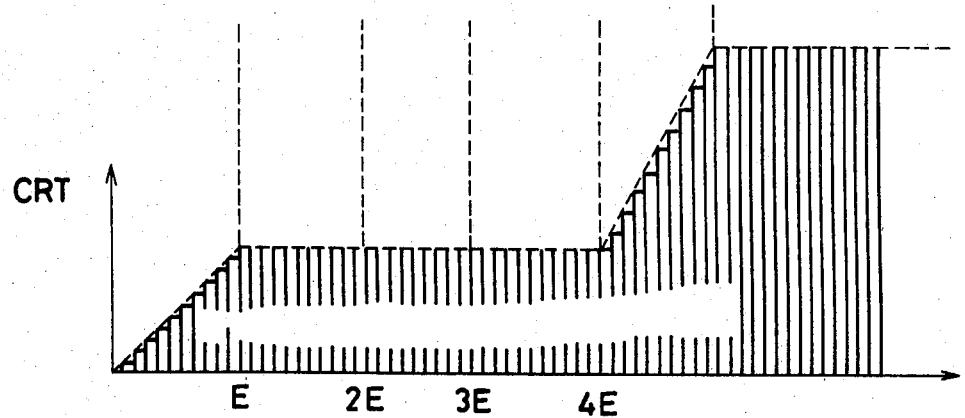
FIG.17

4,402,326

OCCLUSION PRESSURE IMAGE SYSTEM

BACKGROUND OF THE INVENTION

1. Field of the Invention

This invention relates to a novel occlusion pressure image display system which is designed to make visual display of occlusion pressure information in the form of a CRT image by combining a CRT display unit with a novel occlusion pressure sensor capable of converting occlusion pressure information into an electric signal.

2. Prior Art

As a means of ascertaining occlusion pressure distribution, occluding paper (similar to a carbon paper in copying), an occluding ribbon (similar to an inked ribbon for typewritter), or occluding wax (a thin shaping wax sheet) having heretofore been used; but since they are used for ascertaining occlusion pressure distribution on the basis of the physical marks, such as occluding spots produced by occlusion pressure or color transferred onto an occlusion surface, strength of color, or patterns of occluding paper, dents in occluding paper, it is possible to have general knowledge of occlusion pressure but it is impossible to know exact distribution of relative strength in occlusion pressure. Accordingly, it was considered impossible to know that change in occlusion pressure by effect of time (the time when the teeth begin to come into contact with each other a change by effect of time from the time when the teeth begin to come into contact with each to the time when strong occlusion is produced) which is necessary for checking initial contact in time of occlusion control.

The present inventors previously provided an occlusion pressure sensor constructed to convert occluding points and the occlusion pressure produced at the occluding points into an electric signal by a patient bringing the upper teeth into mesh with the lower teeth.

This invention is, however, designed to make visual display of occlusion pressure information in terms of a CRT image by a combination of a CRT display unit with the occlusion pressure sensor.

SUMMARY OF THE INVENTION

Accordingly, it is an object of this invention to provide a system constructed to make visual display of an output signal of occlusion pressure in terms of a CRT image in real time.

It is another object of the invention to provide a system constructed to make visual display of an output signal of the occlusion pressure sensor in terms of a color CRT image in real time.

In the achievement of these objects, an occlusion pressure image display system is provided, constructed in combination, of a novel occlusion pressure sensor assembled of pressure sensitive blocks, arranged in a plurality of lines for converting pressure information into an electric signal and a raster scanning type CRT display unit having a switching means, which scans the pressure sensitive blocks of the occlusion pressure sensor in synchronism with horizontal and vertical synchronizing signals of CRT.

BRIEF DESCRIPTION OF THE DRAWING

FIGS. 16 through 16c are diagrams respectively illustrating a voltage-hue conversion characteristic;

FIG. 17 is a representation of a relation between the color strength of CRT image in the color CRT display unit and the output of occlusion pressure sensor;

DETAILED DESCRIPTION OF PREFERRED EMBODIMENTS

This invention comprises, in combination, an occlusion pressure sensor and a CRT display unit. First, a description will be given of the structure of the occlusion pressure sensor.

Figure 1:
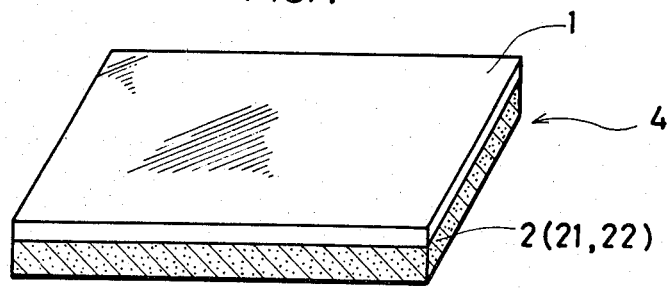
FIG. 1 is a perspective view showing an embodiment of a pressure sensitive element of the occlusion pressure sensor.
Figure 2:
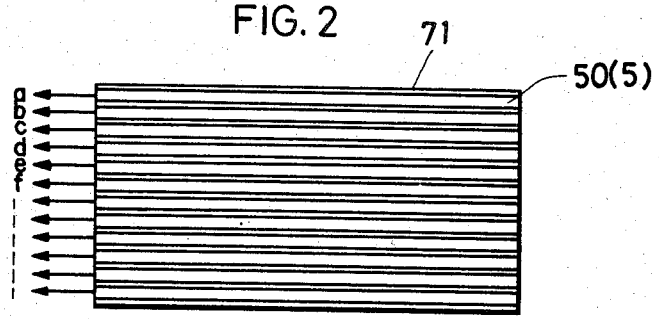
FIGS. 2 and 3 respectively show an arrangement of an upside electrode and an underside electrode of the occlusion pressure sensor shown in FIG. 1.
Figure 3:
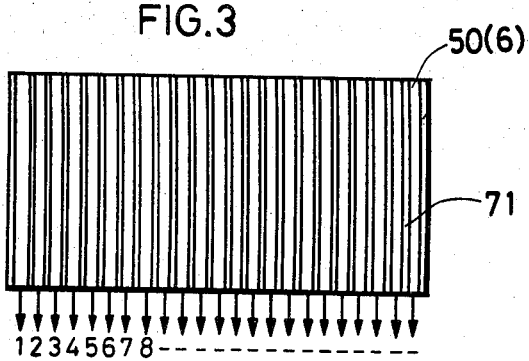
Figure 10:
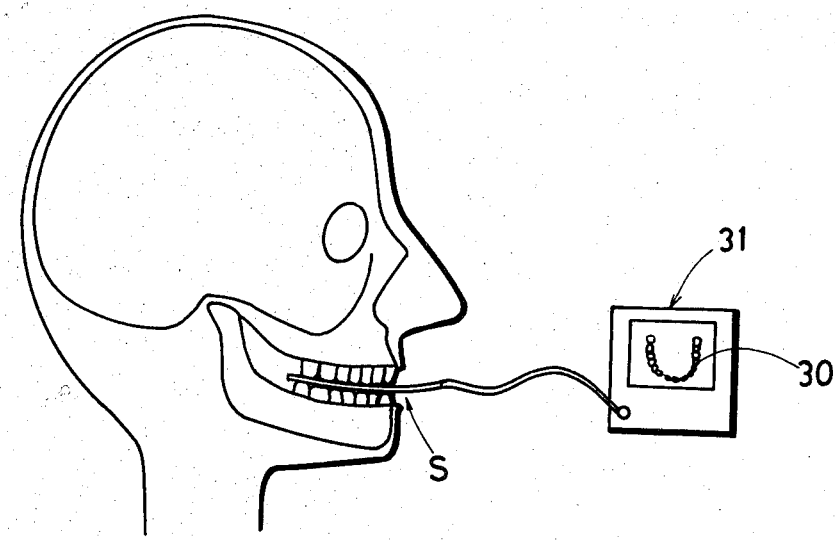
FIG. 10 shows how the invention is used with a patient in dental treatment.

FIGS. 1, 2, 3, 4 illustrate one embodiment of an occlusion pressure sensor, wherein FIG. 1 shows a thin plate-like complex pressure sensitive element 4 constructed of a pressure sensitive layer 2 laminated over the underside of a rectifying layer 1, which pressure sensitive layer 2 changes electric characteristic thereof by being subjected to external pressure. FIGS. 2 and 3 respectively show an arrangement of an upside and underside electrodes constructed in multiple row arrangement, wherein longitudinal strip electrodes 50 . . . are provided in side-by-side relation spaced by insulating materials 71 . . . from one another. The reference characters a, b, c, d, . . . and 1, 2, 3, 4, . . . designated leading-in wires conducted from the strip electrodes 50 . . . . The leading-in wires, as shown in FIG. 10, are housed in one flat insulating tube, conducted out of an occlusion pressure sensor and adapted to conduct occlusion pressure signals in the form of electric signals generated by the occlusion pressure sensor to outside.

Figure 4:
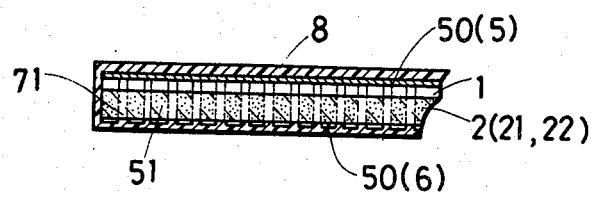
FIG. 4 is a longitudinal sectional view, broken in part, of the occlusion pressure sensor shown in FIG. 1.

According to the occlusion pressure sensor shown in the embodiment, the strip electrodes 50 . . . (5) are arranged and constructed on the upside of the complex pressure sensitive element 4 of the construction shown in FIG. 1 and strip electrodes 50 . . . (5) are arranged and constructed on the underside of the element 4 as shown in FIG. 3 so as to sandwich the element between the electrodes (5) and (6) in the manner that the strip electrodes 50 . . . on the upside and the underside of the element are arranged and constructed in mutually three-dimensionally intersecting relation. Pressure sensitive blocks 51 . . . are constructed in three dimensionally duplicate portion of the strip electrodes 50 . . . on the upside of element 4 and the strip electrodes on the underside thereof, which the element 4 sandwiched therebetween. The numeral 8 designates insulation covering that encircles and envelopes the pressure sensitive element 4. FIG. 4 is a longitudinal sectional view, broken in part, of the occlusion pressure sensor.

Figure 5:
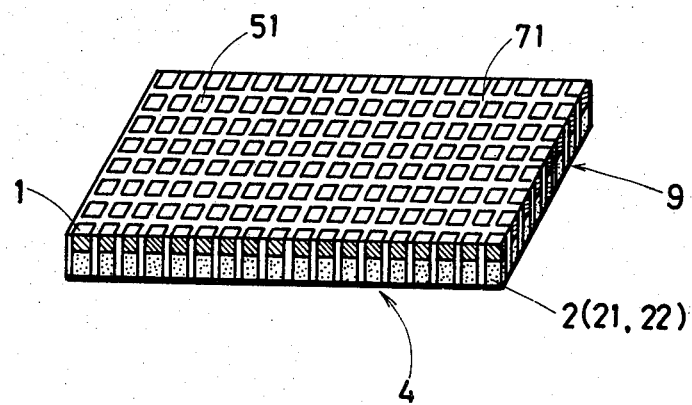
FIG. 5 is a perspective view showing another embodiment of pressure sensitive element of occlusion sensor.

FIGS. 5, 6, 7, 8 illustrate another embodiment of an occlusion pressure sensor, wherein FIG. 5 is a perspective view of another embodiment of the pressure sensitive element. The pressure sensitive blocks 51 . . . according to this embodiment are constructed both by marking off a complex pressure sensitive element of the construction shown in FIG. 1 in lattice form by insulating members 71 . . . and by assembling a plurality of segment electrodes 50 . . . in regularly coordinated relation to both on the upside and on the underside of the thus marked-off portions.

Figure 6:
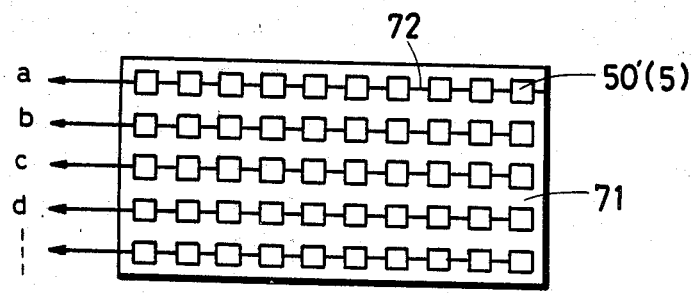
FIGS. 6 and 7 respectively show another embodiment of an upside electrode and an underside electrode of the occlusion pressure sensor shown in FIG. 5.
Figure 7:
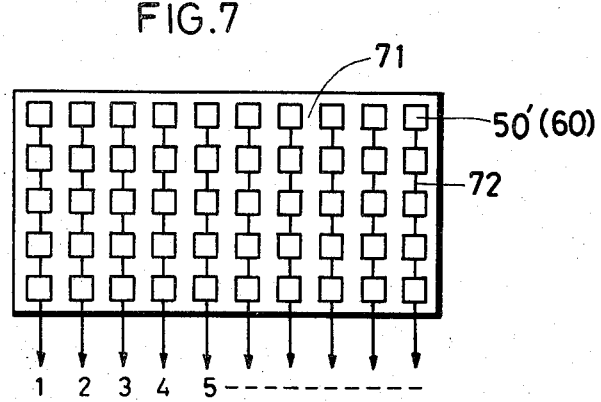

FIGS. 6 and 7 respectively show the arrangement of the upside and underside electrodes arranged on the upside and underside of the complex pressure sensitive element 4 shown in FIG. 4. In the figures, strip electrodes 50' . . . arranged on the upside and underside of the element 4, are respectively connected in series by thin conductors 72 . . . in each file or in each rank arrangement.

Figure 8:
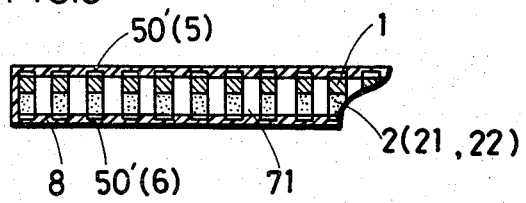
FIG. 8 is a longitudinal sectional view, broken in part, of another embodiment of the occlusion sensor.

FIG. 8 is a longitudinal sectional view, broken in part, of an occlusion pressure sensor, wherein the numeral 8 designates an insulating film encircling and covering the complex pressure sensitive element 4 constructed as above.

In the two embodiments illustrated above, so long as the rectifying layer 1 has the property of permitting the flow of current in one direction; but preventing that of current in the opposite direction, the layer 1, irrespective of whatever material may form the layer, can be selected from all kinds of material or complex such as a selenium rectifying material of Se layer and a complex laminated material Fe consisting of both OdS layer and $Ou_2S$ layer, a selenium rectifying material Al layer and Se layer, a cuprous oxide rectifying material comprising Cu layer and $Cu_2O$ layer, a Schottky rectifying material having a film as of Au, Ni, W, Mo, V formed on the surface Si, Ge or GaAs layer and a semiconductor formed by P-N junction of Si or Ge semiconductor. A material usable as a pressure sensitive layer 2 may be the one 21 (such as VInylidenepolyfluoride film (PVDF), zirconium titanate film (PZT film) or may be the one 22 that changes the electric resistance thereof in response to the external pressure applied (for example all materials such as pressure sensitive rubber possessed with pressure sensitivity by mixing metal or carbon particles into rubber, a film having a pressure resistant effect and in which a semiconductor such as Si is used, a cell containing carbon particles) and other complexes may suitably be selected, so long as they change the electric characteristic thereof under external pressure, no matter whatever material that may be.

On the other hand, the upside electrode 5 and the underside electrode 6 may be formed by direct vapor coating and metallizing an electroconductive metal as of aluminum and silver at suitable points on the respective sides of the pressure sensitive element 4; or may be formed separately by vapor coating or metallizing an electroconductive material such as aluminum and silver on an insulating substrate such as of ceramic and synthetic resin. In short, recourse may be had to any other means that is sufficient to constitute pressure sensitive blocks 51 . . . containing pressure sensitive element 4 and marked off in lattice form.

Figure 9:
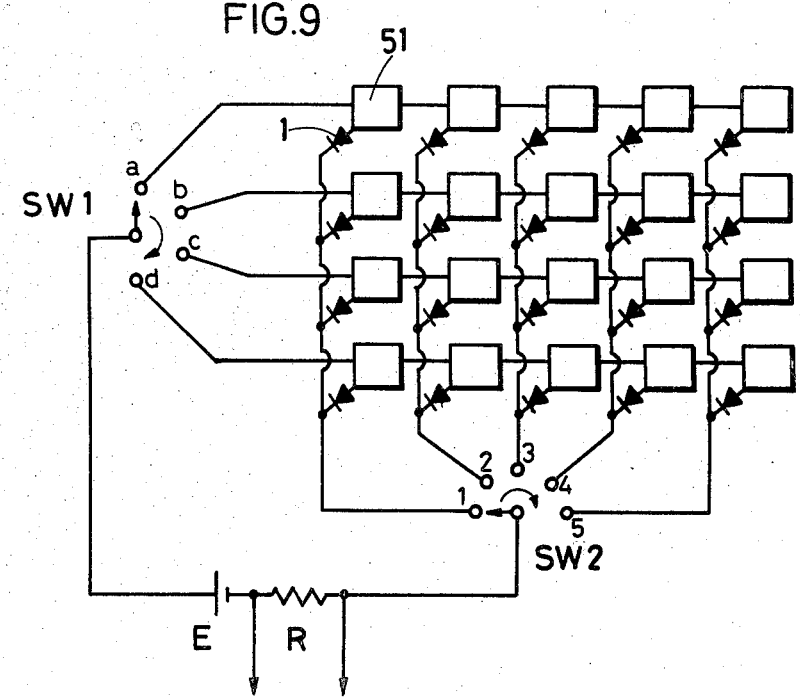
FIG. 9 shows an electrically equivalent circuit of the occlusion sensor.

FIG. 9 is an equivalent typical electric circuit diagram showing electrical structure of the sensor constructed as above, wherein the numeral 51 designates pressure sensitive blocks and 1 designates diodes which equivalently show a rectifying layer.

The structure of the occlusion pressure sensor is electrically shown in the form of the diode matrix of the type described above. In order to derive occlusion pressure information from the sensor, a user bites a sensor S between the upper and lower teeth in the mouth 2; as shown in FIG. 10. In this state, all that is necessary to do is to electrically scan all the pressure sensitive blocks 51 . . . by a combination of changeover operation of switching mechanism SW1 and SW2; as shown in FIG. 9. An occlusion pressure signal is outputted through a resistor R. In this case, electric scanning is effected by a switching means 110, which may be disposed within a CRT display unit D. The means 110 may be readily achieved by a known electronic switch.

Referring now to the principle of electric scanning by the switching means 110 in conjunction with FIG. 9, during the time that the electrodes connected in each rank out of the upside electrode 5 are energized by changeover operation of SW1 (to be referred to hereinafter as "rank-scanning"), the electrodes connected in each file out of the underside electrode 6 are energized successively (to be referred to hereinafter as "file-scanning"). By so doing, pressure sensitive blocks 51 . . . energized in a lattice form are successively scanned, and a change in electric characteristic effected by occlusion pressure is electrically converted into an electric signal output. Incidentally, if the pressure sensitive layer 2 of the occlusion pressure sensor S is of the contruction in which a piezoelectric effect is used, no DC power source E is necessary.

Now a description will be given of an embodiment of a CRT display unit. The CRT unit may roughly be classified into two types, one being of the type in which, as shown in FIG. 11, the occlusion pressure information detected by the sensor S displayed in the form of a CRT black-and-white image, and the other being of the type in which the information is displayed in the form of a CRT color image.

Figure 11:
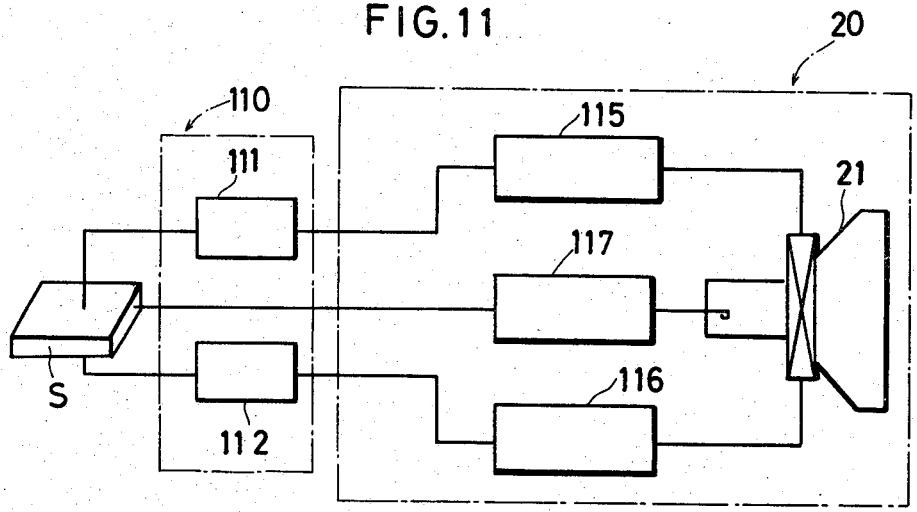
FIG. 11 is a schematic block diagram of a black-and-white CRT display unit.

FIG. 11 is a block diagram showing the circuitry of one embodiment of the CRT black-and-white display unit.

In FIG. 11, a switching means 110, which electrically scans the pressure sensitive blocks 51 . . . of the occlusion pressure sensor S in synchronism which horizontal and vertical synchronizing signals of CRT 21 of the CRT display unit, is provided with an electronic scanning circuit 111 (switching circuit 111) which makes rank-scanning of the pressure sensitive blocks 51 . . . of the sensor S and is provided with an electronic scanning 112 (switching circuit 112) which makes file-scanning of the pressure sensitive block 51 . . . . As shown in FIG.

Figure 13:
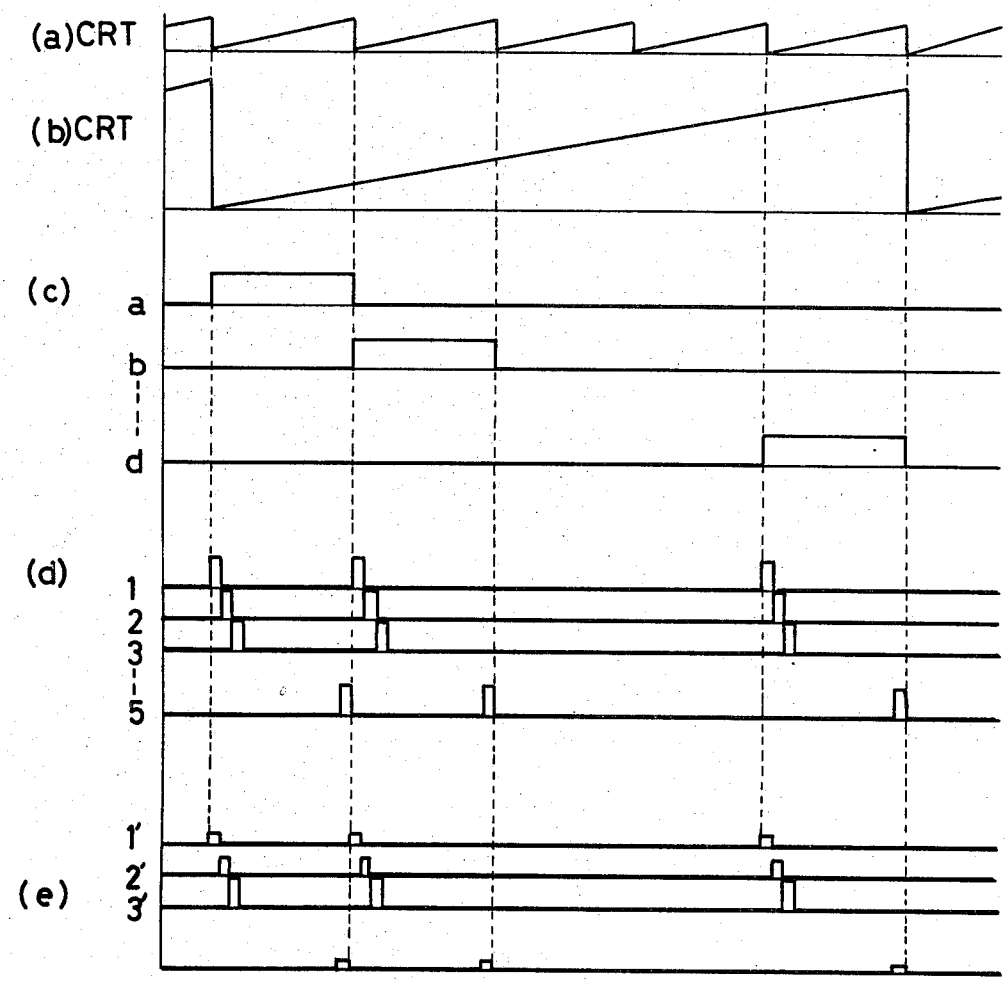
FIG. 13 is a time plot of the rank-scanning, file-scanning, CRT horizontal synchronization and CRT vertical synchronization signals.
Figure 18:
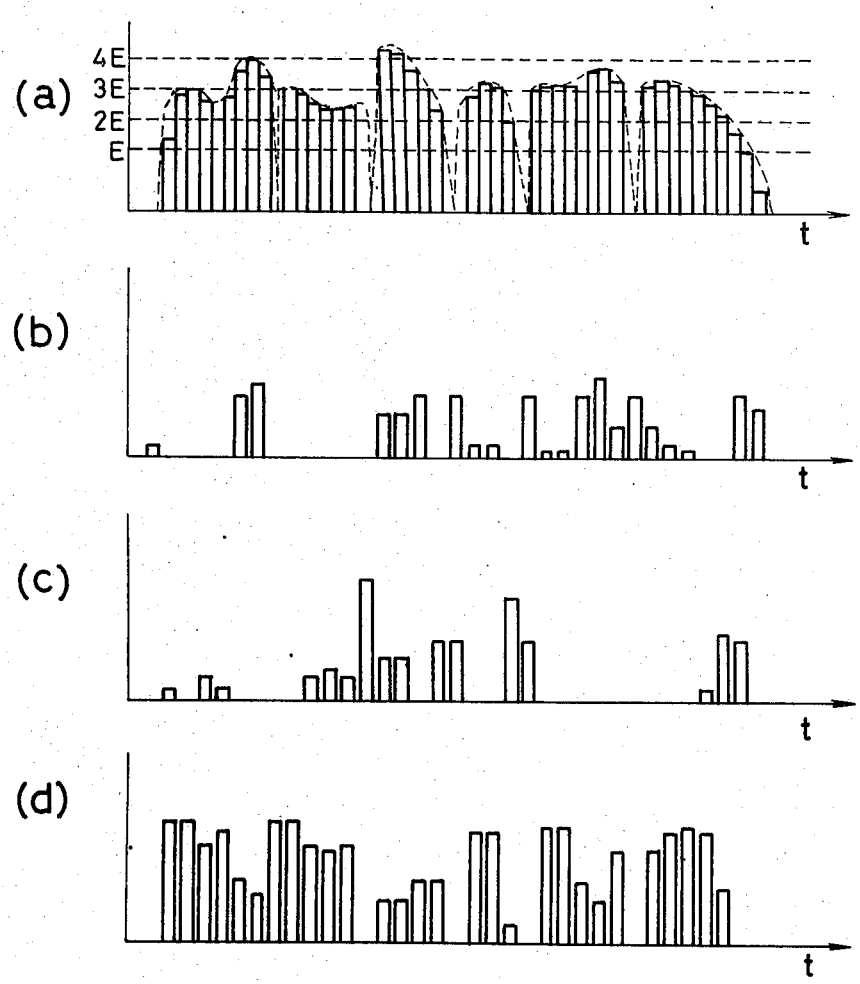
FIG. 18 is a performance characteristics diagram of the hue conversion circuit.
Figure 19:
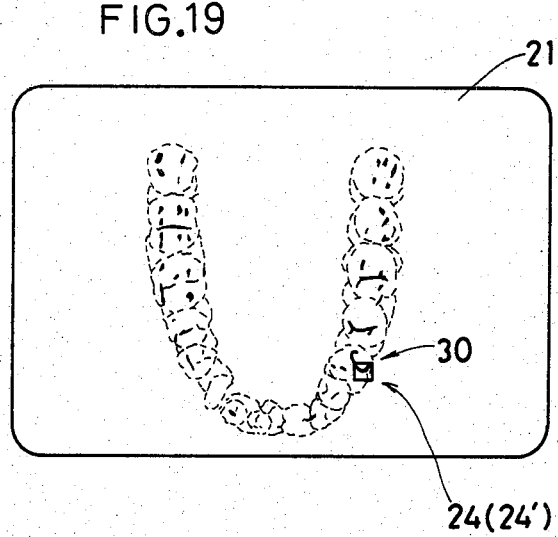
FIG. 19 is a diagram showing occlusion image information displayed on a CRT screen.

13, the rank-scanning and file-scanning are carried out in synchronism with the horizontal and vertical synchronizing signals of CRT 21. The relative occlusion pressure strength signal (FIG. 13) obtained as a result thereof is led to a brilliance modulation circuit 117. As will readily be understood, the occlusion pressure information on the entire jaws as shown in FIG. 18 can be displayed in the form of an image which represents information whose brilliance is responsive to the strength of occlusion pressure.

Figure 12:
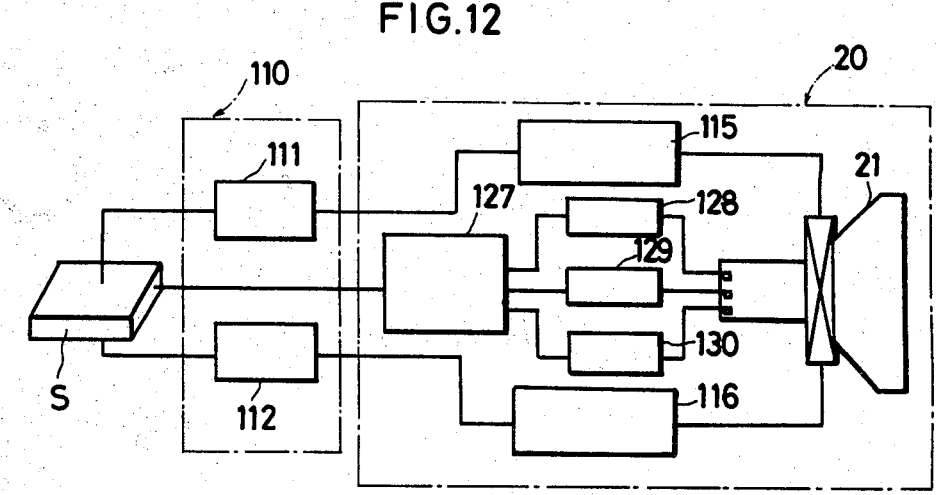
FIG. 12 is a schematic block diagram of a color CRT display unit.

FIG. 12 is a block diagram illustrating the circuitry of one embodiment of CRT display unit which displays information on occlusion pressure from the occlusion pressure sensor S in the form of a CRT color image.

In this case, instead of an occlusion pressure sensor output signal (occlusion pressure relative strength signal) (FIG. 13e) outputted from the occlusion pressure sensor S being led to a brilliance modulation circuit 117, a voltage-hue conversion circuit is used. According to this procedure, the occlusion pressure relative strength signal passes through the voltage-hue conversion 127 (indicates voltage-hue conversion characterstics as in FIGS. 16a–16c, for example, when the occlusion pressure sensor output as shown in FIG. 18a is inputted into the voltage-hue conversion circuit, the red, green and blue signals are generated as shown in FIGS. 18b–18d) which generates a drive signal for subsequent step color drive signal generating circuits 128, 129 and 130 in accordance with the value of voltage of the occlusion pressure relative strength signal and thereafter energizes the color drive signal generation circuits 128, 129 and 130 to thereby give forth the three primary color dots of red, green, blue, with the result that a brilliance spot image having hues responsive to the occlusion pressure shown in FIG. 17 is displayed on the color CRT 21 screen by a combination of the dots.

Figure 14:
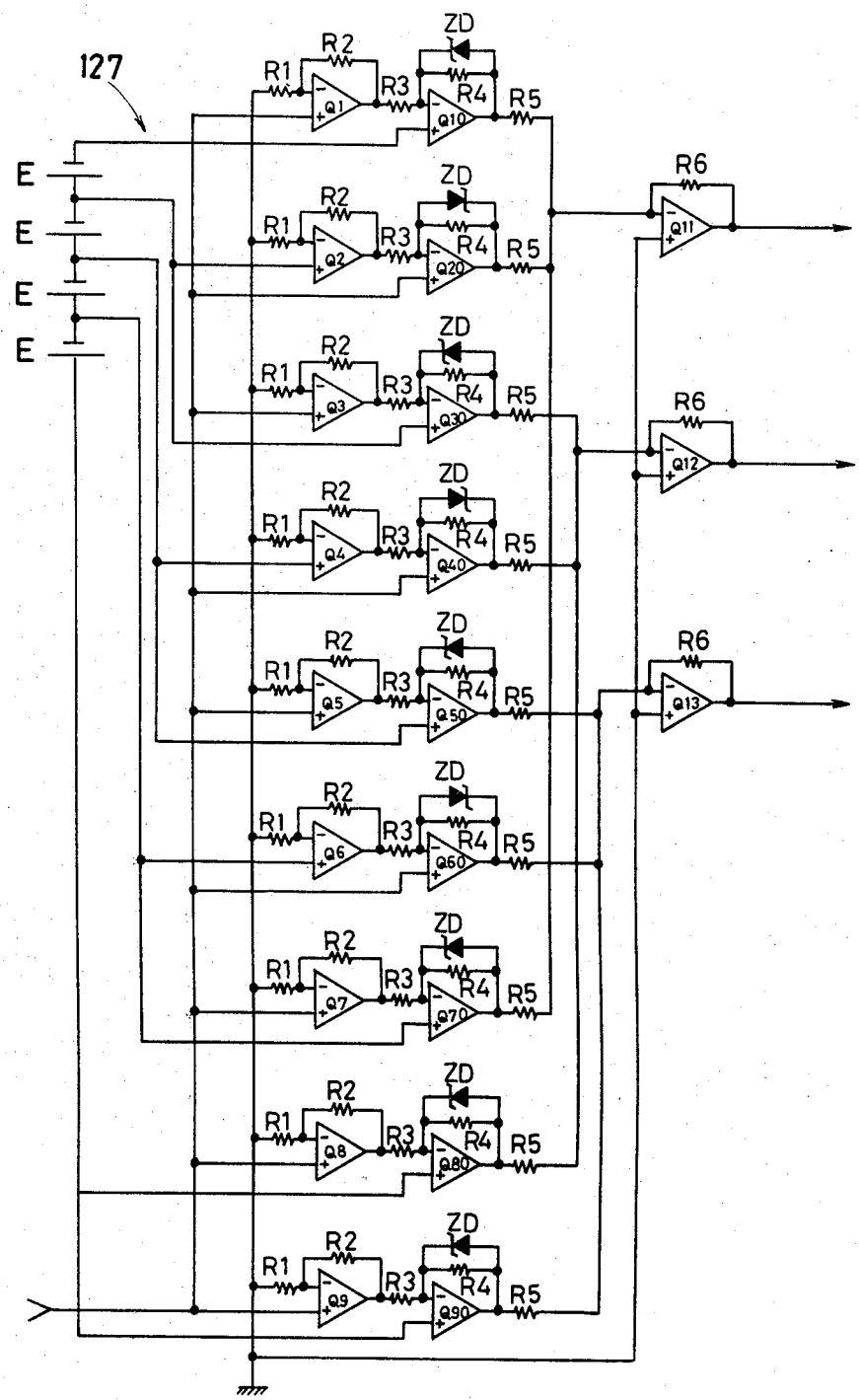
FIGS. 14 and 15 show one embodiment of a hue conversion circuit.

FIG. 14 shows one embodiment of the voltage-hue conversion circuit. In the figure, the character E is a DC power source for setting reference input voltage (differential bias voltage) of a differential amplifier constructed of two operational amplifiers $Q_1$–$Q_{10}$, $Q_2$–$Q_{20}$, ... $Q_9$–$Q_{90}$. Referring now to the differential amplifier made up of the two operational amplifiers, $Q_1$ has an amplification degree of $1+R_2/R_1$ for its non-inversional input and $Q_{10}$ has an amplification degree of $-R_4/R_3$ and has an amplification degree of $1+R_4/R_3$ for its non-inversional input. If $R_4/R_3 = A = R_1/R_2$, the output of $Q_1$ is inputted as inversional output of $Q_{10}$, with the result that the output of $Q_{10}$ for non-inversional input of $Q_1$ provides $$\left(1 + \frac{1}{A}\right)$$

$X(-A) = -(1+A)$, and the non-inversional input of $Q_{10}$ becomes $(1+A)$.

Accordingly, the operational amplification circuit constructed in pairs of $Q_1$ and $Q_2$, has a function as a complete differential amplifier which amplifies an amount of difference between the non-inversional input of $Q_1$ and the non-inversional feedback resistors $R_4$ of $Q_{20}$, $Q_{40}$, $Q_{60}$, clip the output of $Q_{20}$, $Q_{40}$, $Q_{60}$ with plus zenor voltage and zenor diodes ZD connected in parallel to feedback resistors $R_4$ of $Q_{10}$, $Q_{30}$, $Q_{50}$, $Q_{70}$, $Q_{80}$, $Q_{90}$ clip the output of $Q_{10}$, $Q_{30}$, $Q_{50}$, $Q_{70}$, $Q_{80}$, $Q_{90}$ with minus zenor voltage. These zenor diodes ZD have the same characteristics (the same zenor voltage).

Accordingly, the operational amplifier $Q_1$–$Q_{10}$ constructed in pairs, $Q_2$–$Q_{20}$, $Q_3$–$Q_{30}$, $Q_4$–$Q_{40}$, $Q_5$–$Q_{50}$, $Q_6$–$Q_{60}$, $Q_7$–$Q_{70}$, $Q_8$–$Q_{80}$, and $Q_9$–$Q_{90}$ operate respectively as an inversional amplifier of differential bias O (V), a non-inversional amplifier of differential bias E (V), an inversional amplifier of differential bias E (V), a non-inversional amplifier of differential bias 2E (V), an inversional amplifier of differential bias 2E (V), a non-inversional amplifier of differential bias 3E (V), an inversional amplifier of differential bias 3E (V), an inversional amplifier of differential bias 4E (V) and an inversional amplifier of differential bias 4E (V) with input and output voltage characteristics as shown in FIGS. $21_1$–$21_9$. Furthermore, the inversional amplifier $Q_{11}$ synthesizes and inputs the output of differential amplifier constructed of inversional amplifiers $Q_1$–$Q_{10}$, $Q_2$–$Q_{20}$, $Q_7$–$Q_{70}$ through resistors $R_5$, while inversional amplifier $Q_{12}$ synthesizes and inputs the output of differential amplifier constructed of inversional amplifiers $Q_3$–$Q_{30}$, $Q_4$–$Q_{40}$, $Q_7$–$Q_{70}$ through resistors $R_5$, and simultaneously the inversional amplifier $Q_{13}$ synthesizes and inputs the output of differential amplifier constructed of $Q_5$–$Q_{50}$, $Q_6$–$Q_{60}$, $Q_9$–$Q_{90}$ through resistor $R_5$, whereby the inversional amplifiers $Q_{11}$, $Q_{12}$, $Q_{13}$ convert the thus synthesized inputs respectively into red, green, and blue drive signals.

Accordingly, when output voltage from the occlusion pressure sensor is inputted into the input terminal of the voltage-hue conversion circuit 127, the output voltages shown in FIGS. $21_1$–$21_9$ are respectively outputted from operational amplifiers $Q_{10}$, ... $Q_{90}$ in response to theoutput voltage of the occlusion pressure sensor, the output voltages thus outputted are respectively inputted into amplifiers $Q_{11}$, $Q_{12}$ and $Q_{13}$ and inverted with a suitable amplification degree, and are converted into red, green and blue drive signals shown in FIGS. $16_a$–$16_c$.

Figure 15:
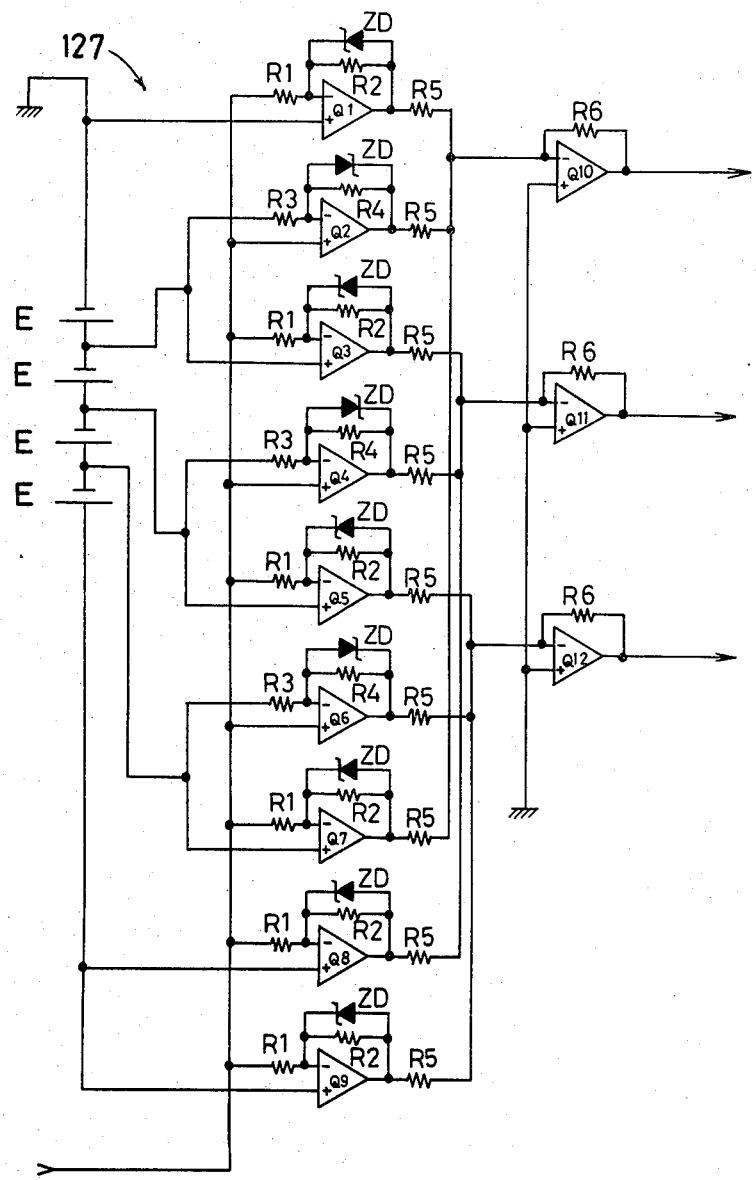

FIG. 15 shows another embodiment of the voltage-hue conversion circuit. If, in this circuit, the relation between the amplification degree $R_2/R_1$ of inversion amplifiers $Q_1$, $Q_3$, $Q_5$, $Q_7$, $Q_8$ and $Q_9$, and amplification degree $1+R_4/R_3$ of non-inversional amplifiers $Q_2$, $Q_4$ and $Q_6$ is represented by equation $R_2/R_1 = 1+R_4/R_3$, the voltage-hue conversion circuit shows functions in a manner similar to that in FIG. 14.

Figure 20:
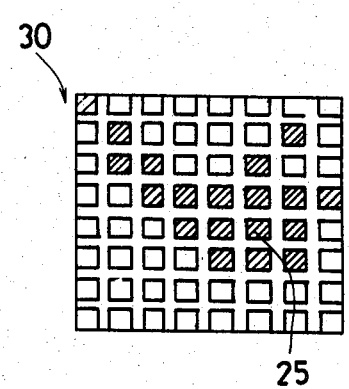
FIG. 20 is an enlarged segmentary view of the portion designated at 30 in FIG. 19.
Figure 21:
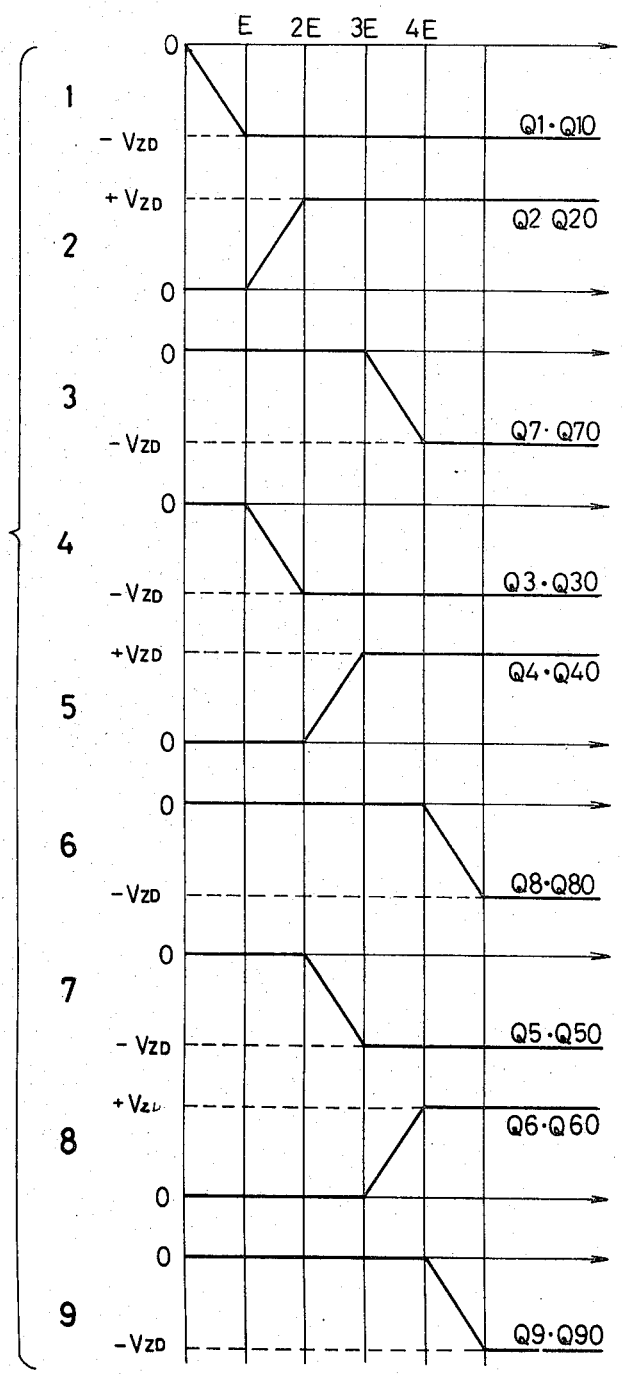
FIG. 21 is a performance of operational amplifier constituting the hue conversion circuit.

Referring to the operating principle of the voltage-hue conversion circuit, having the operational characteristic described above, if the output signals (occlusion pressure signals) outputted from the occlusion pressure sensor S are as shown in FIG. 18a, the occlusion pressure signals are separated into red, green, and blue drive signals as shown in FIGS. 18b–18d in accordance with conversion characteristics in FIGS. 15a–15c, respectively in response to the values of reference input voltages E, 2E, 3E and 4E of the voltage-hue conversion circuit 127 and are respectively inputted into red, green, and blue signal drive circuits 128, 129 and 130. As a result, the red, green and blue signal drive circuits 128, 129 and 130 modulate electronic beams in accordance with the strength of the drive signals produced on the fluorescent screen of CRT 21 synthetic color display (brilliance spot image of color) having the three primary colors of light synthesized in the form of red, green and blue, as shown in FIG. 17. In this manner, the occlusion pressure information on the entire teeth is converted into brillance spot information shown at 25 in FIG. 20, and having hues of strength responsive to the occlusion pressure, and is displayed momentarily on the screen of CRT 21.

As described above, since the invention makes it possible to make correct visual display of the occluding state of the entire teeth in the form of CRT image, having brillance or hue responsive to the occlusion pressure of the teeth, it enables the user to momentarily watch the occluding state in any desired point of the teeth in real time. Accordingly, the invention provides a very useful effect on dental treatment, in that it makes it possible to panoramically watch a change in occlusion by effect of time, namely initial contact between the teeth at a glance which change it was impossible to ascertain by the use of an occluding paper piece, occluding ribbon and occluding wax. Additionally, although not shown, it should be understood that connection of the electric signal or CRT drive signal derived from the occlusion pressure sensor through a memory circuit, VTR and the like, to the system of the invention, makes it possible to display the occlusing state of the teeth also, in the form of momentary stop of image and low-motion image.

What is claimed is:

1. An occlusion pressure image display system designed to make visual display of the occlusion pressure signals detected by an occlusion pressure sensor, said system comprising an occlusion pressure sensor and a CRT display unit, said sensor comprising:
(a) a complex pressure sensitive element, including a rectifying layer and a pressure sensitive layer, said element changing electric characteristic thereof in response to occlusion pressure by detecting the occlusion pressure of the teeth;
(b) an upside electrode and an underside electrode, said electrodes being constructed by arranging thin strip pieces or segments in such manner that said strip pieces or segments are arranged in regularly crossing or coordinated relation vertically of said pressure sensitive element on the upside and underside of the element, so as to form a plurality of pressure sensitive blocks marked off from one another on the pressure sensitive element;
(c) an insulating film enveloping said element inclusive of said upside and underside electrodes; and
(d) a switching means constructed to lead the occlusion pressure signal detected by said sensor to said CRT display unit by electrically scanning said pressure sensitive blocks of said sensor in synchronism with horizontal and vertical signals of CRT.

2. A system according to claim 1, wherein said CRT display unit includes a brillance modulation circuit to thereby lead the occlusion pressure signals of said occlusion pressure sensor to the brilliance modulation circuit so as to display brilliance spot information responsive to occlusion pressure on a CRT screen.

3. A system according to claim 2, wherein said CRT display unit includes a hue conversion circit to thereby lead the occlusion pressure signals of said occlusion pressure sensor to the hue conversion circuit so as to display brilliance information on the predetermined hue in accordance with the strength of occlusion pressure on a CRT screen.

4. A system according to claim 1, wherein the complex pressure sensitive element 4 of said occlusion pressure sensor S comprises a piezoelectric layer 2 laminated over a rectifying layer 1.

5. A system according to claim 2, wherein the complex pressure sensitive element 4 of said occlusion pressure sensor S comprises a piezoelectric layer 2 laminated over a rectifying layer 1.

6. A system according to claim 3, wherein the complex pressure sensitive element 4 of said occlusion pressure sensor S, comprises a piezoelectric layer 2 laminated over a rectifying layer 1.

7. A system according to claim 1, wherein the complex pressure sensitive element 4 constituting said occlusion pressure sensor S, comprises a pressure sensitive resistant layer 22 laminated over a rectifying layer 1.

8. A system according to claim 2, wherein the complex pressure sensitive element 4 constituting said occlusion pressure sensor S, comprises a pressure sensitive resistant layer 22 laminated over a rectifying layer 1.

9. A system according to claim 3, wherein the complex pressure sensitive element 4 constituting said occlusion pressure sensor S comprises a pressure sensitive resistant layer 22 laminated over a rectifying layer 1.

10. A system according to claim 4, 5 or 6, wherein the piezeoelectric layer 21 constituting the complex pressure sensitive element 4 of said occlusion pressure sensor S is made of piezeoelectric rubber.

11. A system according to claim 7, 8 or 9, wherein the pressure sensitive resistant layer 22 constituting the complex pressure sensitive element 4 of said occluding pressure sensor S is made of pressure sensitive rubber.

12. A system according to claim 1, wherein the rectifying layer 1 constituting the complex pressure sensitive element 4 of said occlusion pressure sensor S is made of a selenium rectifying material.

13. A system according to claim 2, wherein the rectifying layer 1 constituting the complex pressure sensitive element 4 of said occlusion pressure sensor S is made of a selenium rectifying material.

14. A system according to claim 3, wherein the rectifying layer 1 constituting the complex pressure sensitive element 4 of said occlusion pressure sensor S is made of a selenium rectifying material.

15. A system according to claim 4, wherein the rectifying layer 1 constituting the complex pressure sensitive element 4 of said occlusion pressure sensor S is made of a selenium rectifying material.

16. A system according to claim 5, wherein the rectifying layer 1, constituting the complex pressure sensitive element 4 of said occlusion pressure sensor S is made of a selenium rectifiying material.

17. A system according to claim 6 wherein, the rectifying layer 1 constituting the complex pressure sensitive element 4 of said occlusion pressure sensor S is made of a selenium rectifying material.

18. A system according to claim 7, wherein the rectifying layer 1 constituting the complex pressure sensitive element 4 of said occlusion pressure sensor S is made of a selenium rectifying material.

19. A system according to claim 8, wherein the rectifying layer 1 constituting the complex pressure sensitive element 4 of said occlusion pressure sensor S is made of selenium rectifying material.

20. A system according to claim 9, wherein the rectifying layer 1 constituting the complex pressure sensitive element 4 of said occlusion pressure sensor S is made of a selenium rectifying material.

21. A system according to claim 1, wherein the rectifying layer 1 constituting the complex pressure sensitive element 4 of said occlusion pressure sensor S is made of Schottky rectifying material.

22. A system according to claim 2, wherein the rectifying layer 1 constituting the complex pressure sensitive element 4 of said occlusion pressure sensor S is made of Schottky rectifying material.

23. A system according to claim 3, wherein the rectifying layer 1 constituting the complex pressure sensitive element 4 of said occlusion pressure sensor S is made of a Schottky rectifying material.

24. A system according to claim 4, wherein the rectifying layer 1 constituting the complex pressure sensitive element 4 of said occlusion pressure sensor S is made of a Schottky rectifying material.

25. A system according to claim 5, wherein the rectifying layer 1 constituting the complex pressure sensitive element 4 of said occlusion pressure sensor S is made of a Schottky rectifying material.

26. A system according to claim 6, wherein the rectifying layer 1 constituting the complex pressure sensitive element 4 of said occlusion pressure sensor S is made of a Schottky rectifying material.

27. A system according to claim 7, wherein the rectifying layer 1 constituting the complex pressure sensitive element 4 of said occlusion pressure sensor S is made of a Schottky rectifying material.

28. A system according to claim 8, wherein the rectifying layer 1 constituting the complex pressure sensitive element 4 of said occlusion pressure sensor S is made of a Schottky rectifying material.

29. A system according to claim 9, wherein the rectifying layer 1 constituting the complex pressure sensitive element 4 of said occulsion pressure sensor S is made of a Schottky rectifying material.

* * * * *